(12) United States Patent
Cullen et al.

(10) Patent No.: US 6,966,888 B2
(45) Date of Patent: Nov. 22, 2005

(54) SINUS VALVED GLAUCOMA SHUNT

(75) Inventors: Cheryl Cullen, Stratford (CA); Lewis H. Marten, Westwood, MA (US)

(73) Assignee: Eagle Vision, Inc., Memphis, TN (US)

( * ) Notice: Subject to any disclaimer, the term of this patent is extended or adjusted under 35 U.S.C. 154(b) by 5 days.

(21) Appl. No.: 10/340,324

(22) Filed: Jan. 13, 2003

(65) Prior Publication Data

US 2003/0135149 A1    Jul. 17, 2003

(51) Int. Cl.[7] .................................................. A61M 5/00
(52) U.S. Cl. ............................................. 604/9; 604/8
(58) Field of Search ........................... 604/8, 9, 27, 28, 604/30, 521, 96.01, 264–7, 294, 289, 299, 604/103.06–103.07, 104, 115, 171; 606/107–9, 606/151, 153, 157, 167, 191, 222–4, 228, 606/233; 600/398–9, 116; 128/898

(56) References Cited

U.S. PATENT DOCUMENTS

| | | | | |
|---|---|---|---|---|
| 3,788,327 A | * | 1/1974 | Donowitz et al. | 604/247 |
| 4,037,604 A | * | 7/1977 | Newkirk | 604/9 |
| 4,402,681 A | * | 9/1983 | Haas et al. | 604/9 |
| 5,127,901 A | * | 7/1992 | Odrich | 604/9 |
| 5,454,796 A | * | 10/1995 | Krupin | 604/294 |
| 6,510,600 B2 | * | 1/2003 | Yaron et al. | 29/428 |
| 6,666,841 B2 | * | 12/2003 | Gharib et al. | 604/8 |

OTHER PUBLICATIONS

Cullen, Cheryl L., Allen, Andrew L., Grahn, Bruce H.; "Anterior chamber to frontal sinus shunt for the diversion of aqueous humor: a pilot study in four normal dogs"; *Veterinary Ophthalonolegists* (1998) 1, 1, pp. 31-39.

* cited by examiner

*Primary Examiner*—Patricia Bianco
(74) *Attorney, Agent, or Firm*—Gordon & Jacobson, P.C.

(57) ABSTRACT

The invention relates to a device and method for treating animals, such as humans and dogs, with primary glaucoma by draining or diverting aqueous humor extraocularly comprising a shunt implant wherein the length and tubing of the shunt ensure fluid flow from the eye directly into the frontal sinus cavity via tubing. The device has crossbeam aids in anchoring the device; four slit valves to control fluid flow at required volume; and bulb that anchors in the frontal sinus cavity. The device is preferably made of medical grade radiopaque silicone rubber, and is flexible. Other improvements and a method for implanting the device are disclosed as well.

56 Claims, 4 Drawing Sheets

SINUS VALVED GLAUCOMA SHUNT

FIELD OF THE INVENTION

The present invention relates generally to the field of glaucoma treatment and glaucoma devices, in particular to a new and useful implantable glaucoma shunt for relieving internal pressure in an animal's eye. More particularly, the present invention provides for a device and method for draining or diverting aqueous humor. Even more particularly, the invention provides for an apparatus and method of preventing postoperative hypotony.

BACKGROUND OF THE INVENTION

Glaucoma is a relatively common ocular disorder in animals. For example, glaucoma has long been recognized as a leading cause of human and canine blindness. The incidence of canine glaucoma, for example, is 0.5%. Increased incidence however is noted in specific breeds. Despite its importance, the long-term control of canine primary glaucoma, whether medical or surgical, continues to elude the veterinary profession.

The current state of the art for long term control of glaucoma in humans and/or dogs and/or other animals (hereinafter, for convenience, sometimes collectively referred to as "animals") includes medical management, cyclophotocoagulation and anterior chamber shunts. For example, anterior chamber implants are used to drain or divert fluids, such as aqueous humor. One of the disadvantages of the art is that implants in dogs fail to maintain normotensive intraocular pressures for more than 6 months postoperatively or do so only when combined with other forms of glaucoma therapy including medical and surgical management. Some implantable glaucoma shunts are simply cylinders that are inserted nearly perpendicularly into the animal's eye and are held by frictional fit by eye tissue. In other words, one of the problems with the art is that the implantable shunts do not remain secure to the site for the purpose of draining or diverting aqueous humor extraocularly. Furthermore, postoperative hypotony occurs when aqueous humor production does not keep pace with outflow. Thus, it is imperative that outflow of aqueous humor be regulated.

Other methods of draining or diverting aqueous humor in dogs have focused on varying implants from valved to nonvalved, and altering explant sites from sclera, subcutaneous, or microvascular, to achieve a route for aqueous drainage.

Studies in humans and dogs indicate that the failure of standard drainage procedures arises mainly due to fibrosis at the site of the filtration bleb and reduced absorptive area for aqueous humor from the scarring, or tube occlusion. Cytokines including fibroblastic growth factor and transforming growth factors $\beta 1$ and $\beta 2$ have been demonstrated in the aqueous humor of dogs and humans with chronic ocular disease including primary glaucoma. These agents have marked mitogenic activity for mesenchymal cells which are responsible for occlusion of these filtering sites. Blocking the effects of these fibroblast stimulating cytokines may inhibit scarring and prevent failure of these filtering procedures. Numerous drugs including mitomycin-C, an antineoplastic, antibiotic agent that reduces collagen production by fibroblasts, have been used to help prevent implant obstruction. Mitomycin-C has yielded some benefit in the success rates of filtration surgeries in humans, monkeys, and rabbits, and has been noted to suppress but not prevent fibrosis around anterior chamber silicone implants in clinically normal dogs.

Many inflammatory diseases are associated with excessive or inappropriate cytokine activity. Cytokines activate lymphocytes and macrophages resulting in a markedly increased production of proteolytic enzymes which rather contribute to the inflammatory process and fibrosis. Intravascular shunting of cytokine-laden aqueous humor may suppress processes and prevent implant fibrosis. Unfortunately implant obstructions, caused by blood reflux, occurred both intraocularly and at the intravascular implant junction. These failures in conjunction with the inability of antineoplastics to prevent fibrosis around implants in dogs attest to the need of shunting aqueous humor to an epithelium-lined site with minimal exposure of mesenchymal tissue. The frontal sinus is an accessible epithelium-lined space and is a potential site for long-term extraorbital diversion of aqueous humor.

Consequently, a need exists in the art for a device and a method for the treatment of glaucoma in animals. A need also exists in the art for draining or diverting aqueous humor extraocularly.

In contrast to the prior art, the present invention provides for a shunt to drain or divert fluids, such as aqueous humor, extraocularly, from the anterior chamber to the frontal sinus via a valve with consistent opening and closing pressures, and to improve frontal sinus implantation and retention via an anchoring bulb and plug stopper.

OBJECTS OF THE INVENTION

Therefore, it is an object of the invention to provide a device and method for treating animals with primary glaucoma.

It is a further objective of the invention to provide a device and method for preventing postoperative hypotony in animals.

It is still another objective of the invention to provide a device and method for the diverting or draining aqueous humor extraocularly, from the anterior chamber to the frontal sinus cavity in animals.

It is still another objective of the invention to provide an implantable shunt that retains its position in the frontal sinus cavity and drains or diverts the aqueous humor extraocularly.

It is still another objective of the invention to provide an implantable shunt that controls the flow of aqueous humor flow at a required volume.

It is still another objective of the invention to provide an implantable shunt that has a bulb wherein when the shunt is tugged back slightly during implantation, the bulb holds the device in position.

It is still another objective of the invention to provide an implantable shunt having a length and tubing to ensure fluid flow from the animal's eye directly into the frontal sinus cavity.

It is a specific object of the invention to provide an aqueous humor shunt device to divert or drain aqueous humor in an animal's eye from the anterior chamber into the frontal sinus cavity, the shunt device comprising a tubing; a crossbeam affixed to the tubing; a bulb molded to the tubing; and at least one slit valve to control fluid flow at a required volume; wherein the length and tubing of the shunt ensure fluid flow from the eye directly into the frontal sinus cavity.

Various other objects, advantages and features of the present invention will become readily apparent from the ensuing detailed description.

SUMMARY OF THE INVENTION

Accordingly, a new device for treating glaucoma is provided comprising implanting a shunt from the anterior chamber to the frontal sinus via a hollow tube. The device is used to divert or drain aqueous humor from the anterior chamber of an animal's eye to help decrease intraocular pressure and thereby control glaucoma.

According to one aspect of the present invention, a shunt device is provided for diverting or draining fluid from an animal's eye from the anterior chamber into the frontal sinus cavity, the shunt device comprising a tubing; a crossbeam affixed to the tubing; a bulb affixed to said tubing; and at least one slit valve, wherein the tubing's length conducts the aqueous humor fluid flow from the anterior chamber of an animal's eye into the frontal sinus cavity.

According to another aspect of the present invention, a method for treating primary glaucoma in an animal comprising implanting in an animal's eye in need thereof an anterior chamber shunt, said shunt comprising: a tubing; a crossbeam affixed to the tubing; a bulb; and a slit valve, wherein the tubing's length ensures aqueous humor fluid flow from the anterior chamber of an animal's eye directly into the frontal sinus cavity.

According to a further aspect of the present invention, a method is provided for preventing postoperative hypotony comprising implanting in an animal's eye in need thereof a shunt, said shunt comprising a tubing; a crossbeam affixed to the tubing; a bulb; and a slit valve, wherein the tubing's length allow for aqueous humor fluid flow from the anterior chamber of an animal's eye directly into the frontal sinus cavity.

The device is an implantable shunt for diverting or draining aqueous humor from the anterior chamber of an animal's eye to the frontal sinus via tubing, having a guide needle at one end thereof, for flushing the shunt preoperatively to ensure slit-valve function and a plug tip at an opposite end of the tubing. The guide needle is removable from the tubing and does not remain in the frontal sinus. Slits are formed at 90° on the tubing adjacent to the plug tip forming a conduit for draining fluid from the anterior chamber of the eye into the frontal sinus. The slits are provided as one-way flow resisting valves in the tubing for allowing a flow of fluid to pass under resistance and in only one direction from the anterior chamber to the frontal sinus, whereby pressure in the anterior chamber is relieved while avoiding excessive outflow of aqueous humor from the anterior chamber. The shape of the device allows easy insertion. Crossbeam aids are affixed to the tubing for anchoring the device to the outside (periosteum) of the frontal sinus. A bulb is molded to the tubing to anchor the shunt in the frontal sinus. When the shunt is tugged back slightly during the surgical procedure, the bulb holds the device in position. The length and the diameter of the tubing ensure fluid flow form the eye directly into the frontal sinus cavity.

These and other embodiments of the invention are provided in or are obvious from the following detailed description of the invention.

BRIEF DESCRIPTION OF THE DRAWINGS

The following detailed description given by way of example, but not intended to limit the invention solely to the specific embodiments described, may best be understood in conjunction with the accompanying drawings in which.

DETAILED DESCRIPTION

The present invention provides an a method for treating primary glaucoma and an anterior chamber shunt device to drain or divert aqueous humor in an animal's eye from the anterior chamber into the frontal sinus cavity, in which the shunt device comprises a first end, adapted to be fitted with a guide needle, to be received within the anterior chamber following removal of the guide needle, and a second end having a crossbeam, bulb, slits and a plug tip to be received within the frontal sinus cavity, wherein the device permits aqueous humor communication from the anterior chamber to the frontal sinus cavity through the slit valves. Fluid communication can be facilitated by intraocular pressure directing the aqueous humor into the slits, as described below.

The embodiments of the present invention can be used to treat animals with primary glaucoma, particularly to drain or divert aqueous humor extraocularly and, more particularly to prevent postoperative hypotony.

Figure 1:
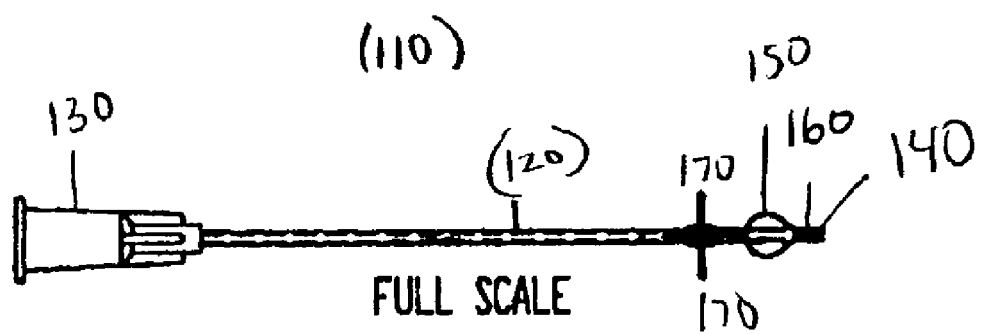
FIG. 1 is a top view of the shunt of the present invention.

Referring now to the drawings, in which like reference numerals are used to refer to the same or similar elements, FIG. 1 shows the glaucoma shunt device (110) of the invention having tubing (120), and a guide needle (130) at a first end thereof, for communicating with the anterior chamber, and a plug tip (140) at an opposite end of the tubing. Guide needle (130) is removed from tubing (120) and does not remain in the sinus. Bulb (150) is connected to tubing (120) and anchors shunt (110) within the frontal sinus cavity. Guide needle (130) does not remain in the sinus. Slits (160) at 90° from bulb (150) to the plug tip (140) form a conduit for draining fluid from the anterior chamber of the eye. Slits (160) are provided as one-way flow resisting valves in the tubing for allowing a flow of fluid to pass under resistance and in only one direction to the frontal sinus, whereby pressure in the anterior chamber is relieved while avoiding excessive outflow of fluid from the anterior chamber. Crossbeam elements (170) are affixed to tubing (120) for anchoring the device to the outside (periosteum) of the frontal sinus.

Higher pressure aqueous humor inside the animal's eye can naturally drain through glaucoma shunt device (110) via slits (160), and tubing (120) to the frontal sinus cavity. Thus, intraocular pressure is relieved.

Figure 2:
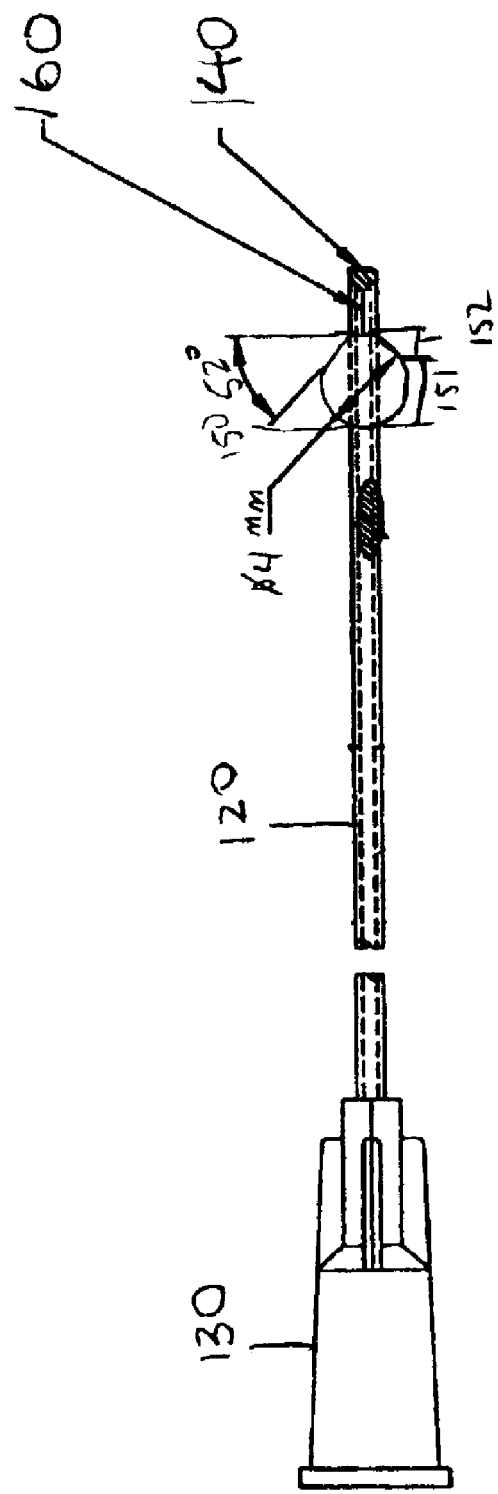
FIG. 2 is a side view of the present invention.

FIG. 2 is a side view of the device. Guide needle (130) can be any conventional guide needle, for example, a 20 or 22 gauge precision guide needle available from Becton Dickinson. The guide needle is friction fitted to tubing (120) and is removable therefrom. The overall length of tube (120) is approximately 60 millimeters, with the proviso that length and tubing of the shunt ensure fluid flow from the eye directly into the frontal sinus cavity. Tubing (120) has an inside diameter of approximately 0.64 millimeters and an outside diameter of approximately 1.2 millimeters. The outer and inner walls form a tubular channel to allow fluid flow from the eye into the frontal sinus cavity. Phantom lines on FIG. 2 display the tubular channel within the device. In all cases the length and the diameter of the tubing (120) must ensure fluid flow from the eye directly into the frontal sinus cavity. Tubing (120) is made of any suitable material known in the art, such as, for example, medical grade radiopaque silicone rubber, and is flexible.

At the opposite end of the device is a plug tip (140). The plug tip is made of any suitable material known in the art, such as, for example, silicone.

Bulb (150) is approximately 3 millimeters from plug tip (140). Bulb (150) is made of any suitable material known in the art, such as, for example, clear silicone. Bulb (150) provides an anchoring aspect to the shunt. Bulb (150) is molded onto tube (140). Bulb (150) has a rounded portion (151) and an angled portion (152). Angled portion (152) forms a straight line at approximately 52° from a line perpendicular to tube (120) and rounded portion (151) has a diameter of approximately 4 mm. The maximum length of bulb (150) is 4 millimeters measured through the tubing.

Slits (160) are formed in the tubing between the end of angled portion (152) of bulb (150) to plug tip (140). Slits (160) are at 90° degrees on the tubing and are approximately 3 millimeters in length. Slits (160) form a conduit for draining fluid from the anterior chamber of the eye into the frontal sinus cavity. Slits (160) provide one-way flow resisting valves in the tubing for allowing a flow of fluid to pass under resistance and in only one direction to the frontal sinus, whereby pressure in the anterior chamber is relieved while avoiding excessive outflow of fluid from the anterior chamber. The slits (160) drain the fluid in the anterior eye at an opening pressure between 18–20 mmHg. The slits (160) arc closed at pressures under 18 mmHg. Thus, the outflow of aqueous humor is regulated at consistent opening and closing pressures and the volume of aqueous humor is controlled. The slits (160) may be adjusted to be open at a different pressure.

Furthermore, the consistent opening and closing pressures prevent postoperative hypotony because the level of volume of aqueous humor is regulated. Any conventional means may be used to test and make the slits (160) in the tubing.

Figure 3:
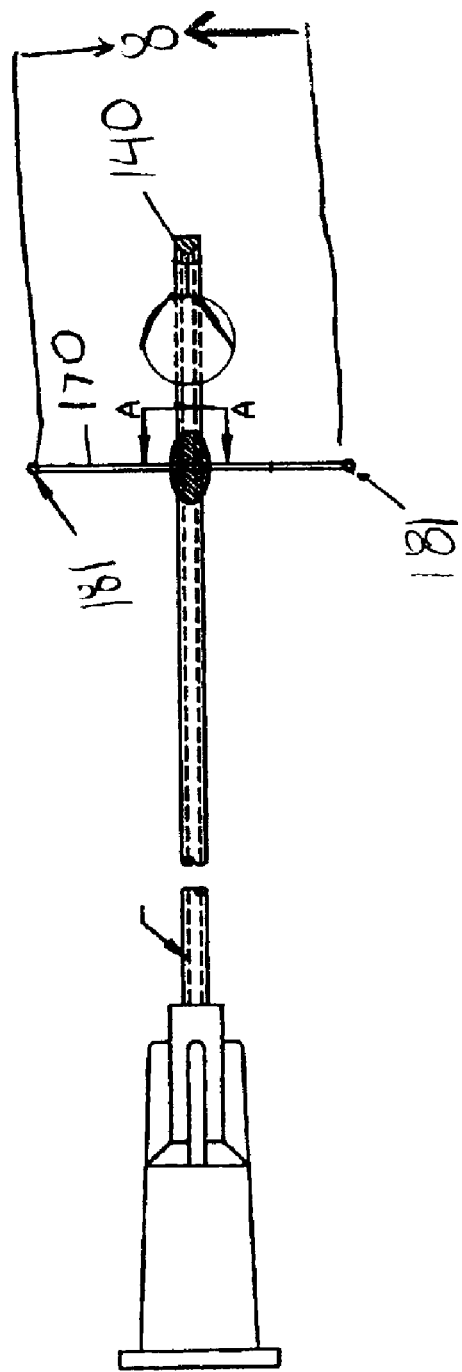
FIG. 3 is a top view of the present invention.

FIG. 3 is a top view of the device with labeled section A—A. Crossbeams (170) with crossbeam ends (181) are provided. The materials used to make crossbeams (170) is made of any suitable material known in the art, such as, for example fluorocarbon suture material. The crossbeams are glued with silicone cement to the tubing approximately 11 millimeters from the plug tip (140) end of the device. However, a skilled artisan would readily understand that there are other ways to secure the crossbeams to the tubing. Crossbeams (170) form a diameter of approximately 11 millimeters measured through the tubing.

Crossbeams (170) help to position device (110) by providing aids for anchoring the device to the outside surface (periosteum) of the frontal sinus. Crossbeams ends (181) further define adhesives to aid in the anchoring. The materials used to make the adhesives are made of any suitable material known in the art, such as, for example medical grade silicone adhesive. The shape of shunt (110) allows easy insertion into the anterior chamber and the frontal sinus cavity and when the shunt is tugged back slightly during suturing the anterior chamber end, the crossbeams (170) and bulb (150) hold device (110) in position.

Figure 4:
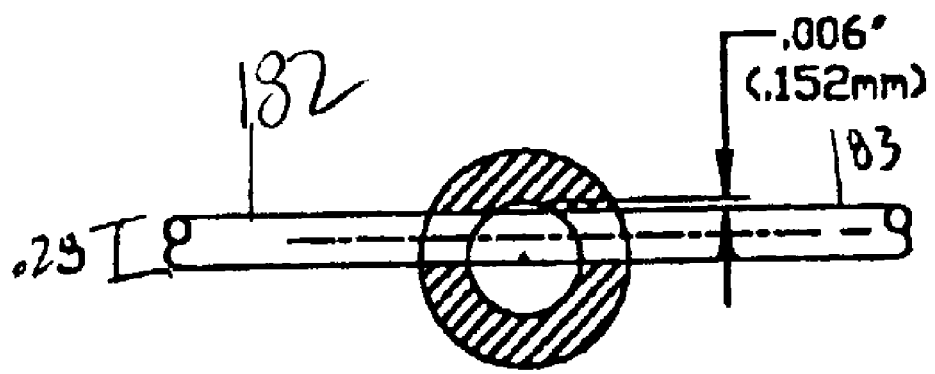
FIG. 4 is the perspective view of A—A on FIG. 3.

FIG. 4 is the perspective view of A—A of FIG. 3. The crossbeams further define left arm (182) and right arm (183). The left and right arms may be any shape and thickness that aids in suturing the device, but preferably are 0.28 millimeters thick. The arms are affixed to the tube approximately 0.152 millimeters from the inner wall of the tubular channel.

Although preferred embodiments of the present invention and modifications thereof have been described in detail herein, it is to be understood that this invention is not limited to those precise embodiments and modifications, and that other modifications and variations may be affected by one skilled in the art without departing from the spirit and scope of the invention as defined by the appended claims.

What is claimed is:

1. A method for treating primary glaucoma in an animal comprising: implanting in the animal's eye a shunt for diverting or draining fluid from an anterior chamber of the animal's eye into a frontal sinus cavity, said shunt including,
   a tubing;
   a crossbeam affixed to the tubing;
   a bulb affixed to said tubing; and
   at least one slit valve,
wherein the tubing extends from the anterior chamber of an animal's eye into the frontal sinus cavity.

2. The method of claim 1, wherein the bulb comprises a straight angled portion and a rounded portion.

3. The method of claim 2, wherein the angled portion is angled 52° from a line perpendicular to the tubing.

4. The method of claim 3, wherein the rounded portion has a diameter of approximately 4 mm.

5. The method of claim 1, wherein the shunt includes a guide needle which is used during said implanting.

6. The method of claim 5, wherein the guide needle is a 20 or 22 gauge needle.

7. The method of claim 1, wherein the animal is a mammal.

8. The method of claim 1, wherein the animal is a human.

9. The method of claim 1, wherein the animal is a dog.

10. The method of claim 1, wherein the crossbeam is sized to be anchored to the periosteum of the frontal sinus.

11. The method of claim 1, wherein the bulb is molded to the tubing.

12. The method of claim 1, wherein the slit valve has consistent opening and closing pressures.

13. The method of claim 1, wherein the slit valve has an opening pressure of 18–20 mmHg.

14. The method of claim 1, wherein the tubing is medical grade radiopaque silicone rubber.

15. The method of claim 1, wherein the tubing has an inner diameter of 0.64 millimeters and an outside diameter of 1.2 millimeters.

16. The method of claim 1, wherein the bulb is clear silicone.

17. The shunt of claim 1, wherein the crossbeam is fluorocarbon suture material.

18. The method of claim 1, wherein when the shunt is tugged back slightly during implantation, the bulb holds the device in position.

19. The method of claim 1, wherein the crossbeam is cemented to the tubing.

20. The method of claim 1, wherein the crossbeam is approximately 11 millimeters in diameter measured through the tubing.

21. The method of claim 1, wherein the tubing has a length of approximately 60 mm.

22. A method for treating primary glaucoma in an animal comprising:
   implanting in the animal's eye a shunt for diverting or draining fluid from an anterior chamber of the animal's eye into a frontal sinus cavity, said shunt including, a tubing;

a crossbeam affixed to the tubing;

a bulb having a front side which defines a constant angle and a rear rounded portion which is curved along a constant radius; and a slit valve, wherein the tubing extends from the anterior chamber of an animal's eye directly into the frontal sinus cavity.

23. The method of claim 22, wherein the shunt further includes a guide needle used during said implantating.

24. The method of claim 23, wherein the guide needle is a 20 gauge needle.

25. The method of claim 22, wherein the angle portion is 52° from a line perpendicular to the tubing.

26. The method of claim 25, wherein the rounded portion has a diameter of approximately 4 mm.

27. The method of claim 22, wherein the shunt is anchored to the periosteum of the frontal sinus.

28. The method of claim 22, wherein the bulb is molded to the tubing.

29. The method of claim 22, wherein the slit valve has consistent opening and closing pressures.

30. The method of claim 22, wherein the slit valve has an opening pressure of 18–20 mmHg.

31. The method of claim 22, wherein the tubing is medical grade radiopaque silicone rubber.

32. The method of claim 22, wherein the tubing has an inner diameter of 0.64 millimeters and an outside diameter of 1.2 millimeters.

33. The method of claim 22, wherein the bulb is clear silicone.

34. The method of claim 22, wherein the crossbeam is fluorocarbon suture material.

35. The method of claim 22, wherein when the shunt is tugged back slightly during implantation, the bulb holds the device in position.

36. The method of claim 22, wherein the crossbeam is cemented to the tubing.

37. The method of claim 22, wherein the crossbeam is approximately 11 millimeters in diameter measured through the tubing.

38. A shunt device for diverting or draining fluid from an animal's eye from the anterior chamber into the frontal sinus cavity, said shunt comprising:

a tubing;

a crossbeam affixed to the tubing;

a bulb affixed to the tubing and longitudinally offset relative to the crossbeam; and a valve.

39. The shunt of claim 38, wherein the bulb comprises an angled portion and a rounded portion.

40. The shunt of claim 39, wherein the angle portion is 52° from a line perpendicular to the tubing.

41. The shunt of claim 40, wherein the rounded portion has a diameter of approximately 4 mm.

42. The shunt of claim 38, further comprising a guide needle.

43. The shunt of claim 42, wherein the guide needle is a 20 or 22 gauge needle.

44. The shunt of claim 38, wherein the shunt is anchored to the periosteum of the frontal sinus.

45. The shunt of claim 38, wherein the bulb is molded to the tubing.

46. The shunt of claim 38, wherein the slit valve has consistent opening and closing pressures.

47. The shunt of claim 38, wherein the slit valve has an opening pressure of 18–20 mmHg.

48. The shunt of claim 38, wherein the tubing is medical grade radiopaque silicone rubber.

49. The shunt of claim 38, wherein the tubing has an inner diameter of 0.64 millimeters and an outside diameter of 1.2 millimeters.

50. The shunt of claim 38, wherein the bulb is clear silicone.

51. The shunt of claim 38, wherein the crossbeam is fluorocarbon suture material.

52. The shunt of claim 38, wherein when the shunt is tugged back slightly during implantation, the bulb holds the device in position.

53. The shunt of claim 38, wherein the crossbeam is cemented to the tubing.

54. The shunt of claim 38, wherein the crossbeam is approximately 11 millimeters in diameter measured through the tubing.

55. A shunt according to claim 38, wherein the valve is a slit valve.

56. A shunt according to claim 38, wherein the tubing has a length sufficient to permit aqueous humor flow from the anterior chamber of an animal's eye directly into the frontal sinus cavity.

* * * * *